United States Patent [19]
Carlisle

[11] Patent Number: 5,687,831
[45] Date of Patent: Nov. 18, 1997

[54] FLEXIBLE PARTS FEEDER

[75] Inventor: Brian R. Carlisle, Palo Alto, Calif.

[73] Assignee: Adept Technology, Inc., San Jose, Calif.

[21] Appl. No.: 428,679

[22] Filed: Apr. 25, 1995

Related U.S. Application Data

[63] Continuation-in-part of Ser. No. 124,662, Sep. 22, 1993, abandoned.

[51] Int. Cl.$^6$ .................................................... B65G 47/24
[52] U.S. Cl. .................................................. 198/395; 198/396
[58] Field of Search .................................. 198/395, 396, 198/431, 443, 444, 580, 468.6, 550.2, 603, 394, 577

[56] References Cited

U.S. PATENT DOCUMENTS

| | | |
|---|---|---|
| 2,877,884 | 3/1959 | Esenwien . |
| 3,823,815 | 7/1974 | Bretten et al. . |
| 3,848,724 | 11/1974 | Belk ............................ 198/431 |
| 3,881,605 | 5/1975 | Grossman . |
| 4,014,460 | 3/1977 | Bryan ........................... 198/396 |
| 4,164,279 | 8/1979 | Dubuit ........................ 198/468.6 |
| 4,262,793 | 4/1981 | Hebenstreit et al. ............ 198/431 |
| 4,284,187 | 8/1981 | Kramer et al. . |
| 4,465,174 | 8/1984 | Uhl . |
| 4,678,073 | 7/1987 | Anderson et al. ............... 198/394 |
| 4,690,266 | 9/1987 | Croman et al. . |
| 4,697,689 | 10/1987 | Carrell .......................... 198/396 |
| 4,811,831 | 3/1989 | Honkomp et al. ............... 198/394 |

(List continued on next page.)

FOREIGN PATENT DOCUMENTS

| | | |
|---|---|---|
| 2632480 | 12/1989 | France . |
| 3817465 | 11/1989 | Germany . |
| 56-98155 | 8/1981 | Japan . |
| WO 92/03364 | 3/1992 | WIPO . |

OTHER PUBLICATIONS

Maul, G. P., Goodrich, J.L., A Methodology for Developing Programmable Parts Feeders, IIE Trans., v. 15, No. 4, 1983.

Suzuki, T., Kohno, M., The Flexible Parts Feeder Which Helps a Robot Assemble Automatically, Assembly Automation, v. 1, No. 2, 1981.

Zenger, D., Dewhurst, P., Automatic Handling Of Parts For Robot Assembly, Annals of CIRP, v. 33, No. 1, 184.

Cowart, N.A., et al., Programmable Assembly Research, Technology Transfer To Industry–Phase II, Westinghouse R & D Center, ISP 78–18773, Pittsburgh, 1981.

Kim et al., "A Shape Metric for Design–for–Assembly", May 1992, pp. 968–973, Proceedings of the 1992 IEEE International Conference on Robotics and Automation.

Schimmels et al., "The Robustness of an Admittance Control Law Designed for Force Guided Assembly to the Disturbance of Contract Friction", May 1992, pp. 2361–2366, Proceedings of the 1992 IEEE International Conference on Robotics and Automation.

Rao et al., "Orienting Generalized Polygonal Parts", May 1992, pp. 2263–2268, Proceedings of the 1992 IEEE International Conference on Robotics and Automation.

Farnum, "Delivering the Part", Mar. 1986, Manufacturing Engineering.

Murch et al., "Predicting Efficiency of Parts Orienting Systems", pp. 55–57, Automation, Feb. 1971.

*Primary Examiner*—Joseph E. Valenza
*Attorney, Agent, or Firm*—Oliff & Berridge

[57] ABSTRACT

A parts feeder conveys parts to a selection zone viewed by a vision system, which selects parts having an orientation allowing them to be gripped and transferred from the conveyor. Non-selected parts are conveyed from the selection zone to a hopper for recirculation to the selection zone. The parts are tumbled between successive passes through the selection zone and eventually assume orientations allowing them to be gripped. The gripper has rotatable finger pads which can be either driven or passively rotated.

22 Claims, 9 Drawing Sheets

U.S. PATENT DOCUMENTS

| | | |
|---|---|---|
| 4,819,784 | 4/1989 | Sticht . |
| 4,835,730 | 5/1989 | Shimano et al. . |
| 4,876,728 | 10/1989 | Roth . |
| 4,909,376 | 3/1990 | Herndon et al. . |
| 4,917,562 | 4/1990 | Colli et al. .............................. 198/444 |
| 5,084,959 | 2/1992 | Ando et al. . |
| 5,105,930 | 4/1992 | Spatafora et al. . |
| 5,205,396 | 4/1993 | Grecksch et al. ....................... 198/577 |
| 5,314,055 | 5/1994 | Gordon ................................... 198/395 |
| 5,314,293 | 5/1994 | Carlisle et al. . |

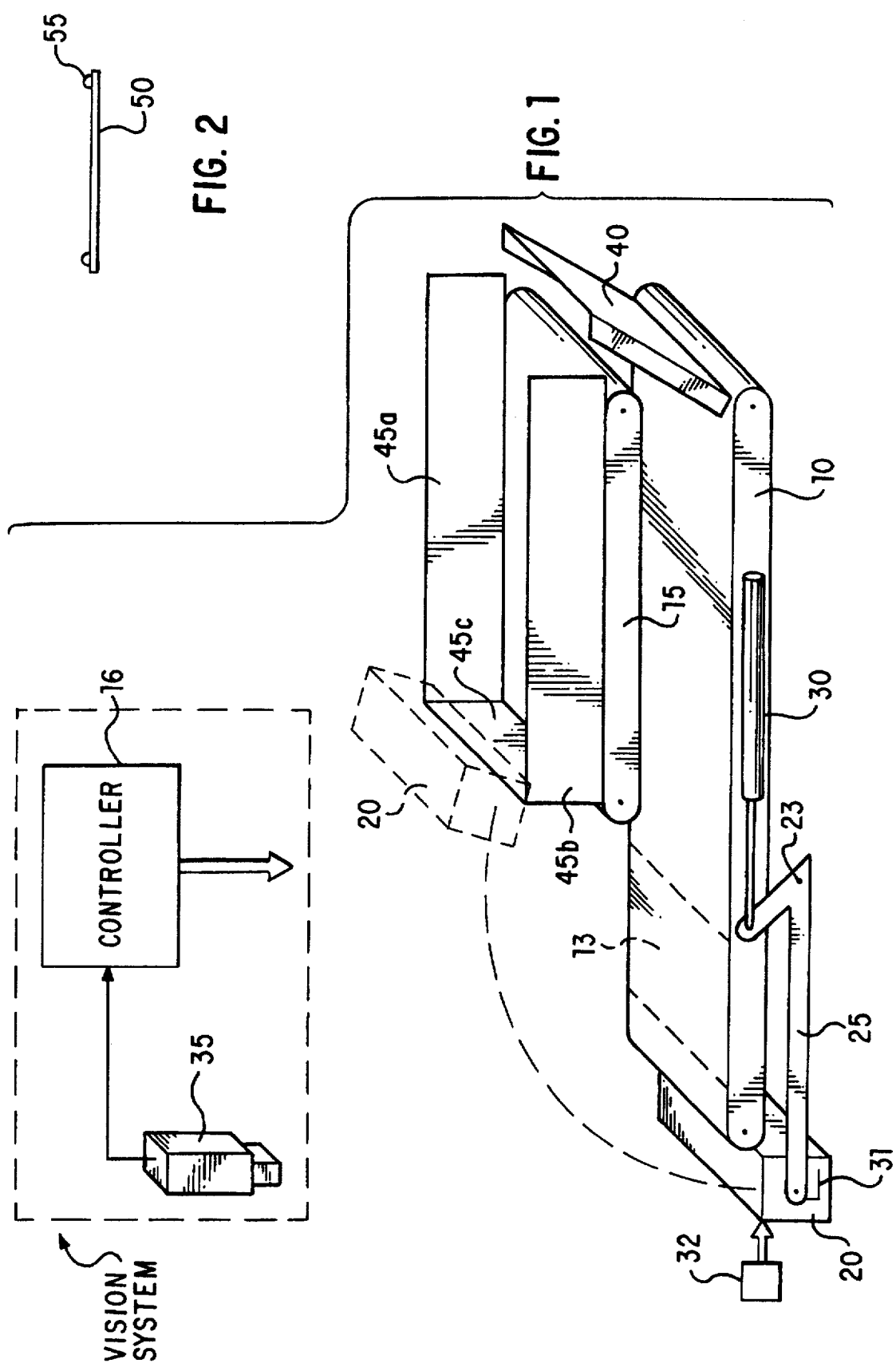

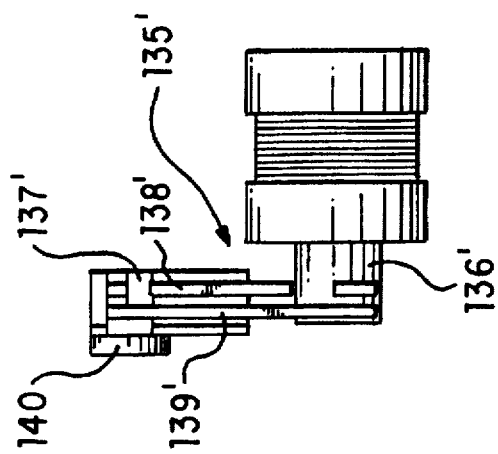
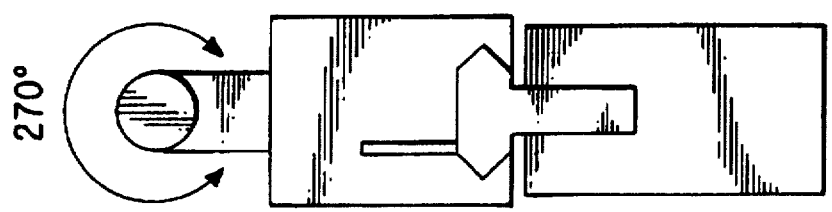
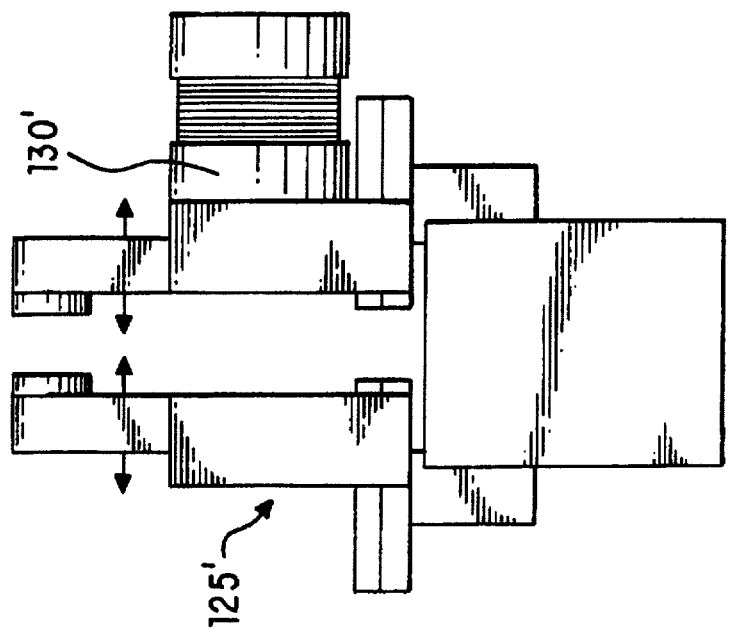
FIG. 8c
FIG. 8b
FIG. 8a

FLEXIBLE PARTS FEEDER

This application is a continuation-in-part of U.S. application Ser. No. 08/124,662, filed Sep. 22, 1993 abandoned.

BACKGROUND OF THE INVENTION

1. Field of the Invention

The invention relates to parts feeders, and more particularly to feeders having a transport system for transporting small, electronic and mechanical parts to a selection zone.

2. Related Art

To automate the assembly of mechanical components, parts must be precisely oriented prior to packing or insertion. The manufacturing industry currently relies on passive parts feeders using hand-crafted mechanical "filters" that admit only those parts having a desired orientation. Rejected parts are recycled for another pass through the orientation mechanism. When part geometry changes, the "filter" must be mechanically redesigned, involving a trial-and-error process typically requiring several months and up to 50% of the costs of the automated assembly cell.

Currently, the most common method for orienting parts is a vibratory bowl feeder, in which parts in a specially configured bowl are vibrated with a rotary motion so that they climb a helical track. As they climb, a sequence of baffles and cut-outs in the track creates a mechanical "filter" that causes parts in all but one orientation to fall back into the bowl for another attempt at achieving a desired orientation. It is also possible to design the track to mechanically rotate parts into a desired orientation. Other orientation methods use centrifugal forces, belts, or reciprocating forks, rather than vibration, to move parts through the part-feeding mechanism.

When part geometry changes in a bowl feeder, specialists must redesign the bowl and/or other components of the mechanism to accommodate the new parts. The mechanism must be tested and modified numerous times to achieve the best feeding efficiency and to eliminate jams.

Another prior art feeder uses an array of nests (silhouette traps) cut into a vibrating plate. The plate and nests vibrate so that parts will remain in the nests only in a particular orientation. By tilting the plate and letting parts flow across it, the nests eventually fill up with parts in the desired orientation. Although the vibratory motion is under software control, specialized mechanical nests must still be designed for each new type of part and jamming is a problem, as with bowl feeders. Several other designs for programmable parts feeders have been proposed, in which programmed vibration is used to drive parts into a stable orientation. These methods are useful for bringing parts into "low-energy" positions and orientations, where their respective centers of mass are as low as possible, but other methods are then required to further orient the parts relative to a selection plane.

Sensors, such as tactile probes, photocells, fiber optic sensors and vision systems, have been used to determine the position and orientation of parts delivered by a vibratory track. Once part position and orientation are determined, air jets and trap doors are used to group parts in similar positions and orientations. Difficult and time-consuming physical changes must be made in the components of such systems when part type changeover is desired.

For decades, researchers have studied the "bin picking" problem, that is, the problem of picking a part out of a bin of jumbled parts. Due to the difficulty of recognizing overlapping parts in arbitrary orientations, few of these systems have been adopted for industrial applications. Standard vision systems, however, are sometimes successful when additional constraints are imposed, such as presenting parts in isolation on a flat surface. U.S. Pat. No. 4,876,728 to Roth, which is incorporated herein by reference, discloses an improved vision system for distinguishing touching parts on a conveyor. The vision system processes binary images and recognizes objects based on boundary features, such as lines, arcs, corners and holes, instead of "blob features." The system is interfaced to a robot system and can recognize up to five parts per second. The ability of the vision system to quickly and reliably recognize parts is still dependent, though, on the orientation and degree of overlap of the parts being inspected.

Unlike bowl feeders, which present parts in their final desired orientation, parts presented on flat conveyor surfaces, such as shown in Roth, may lie in one of several stable states. Typically, these stable states are not the desired final orientation for the parts. In general, the parts may require translation and rotation through six degrees of freedom in order to reach their final orientation and destination. While it is possible to use a conventional six axis robot to acquire parts from the flat conveying surface, in general, such robots are not as cost-effective, fast, or precise as robots having less degrees of freedom. These drawbacks of the six axis robot decreases the overall effectiveness of the parts feeder.

In addition, six axis robots generally have their three axes of rotation of the wrist intersecting at a single point. This results in a substantial distance between these axes of rotation and the tip of the robot fingers due to the volume required by the wrist and the offset for the fingers. This wrist and finger arrangement has the following drawbacks. First, use of this arrangement will require the designation of a substantial area for the part selection zone so that the wrist and finger arrangement can be properly manipulated to pick up a part. This leads to an overly large construction of the parts feeder. Second, because some applications will require, during part pick-up, that the longitudinal axes of the fingers be inclined relative to the conveyor surface in order to properly reposition the part, the ability of the gripper to select a part from among a plurality of parts crowded together may be significantly impaired. Third, because the above wrist and finger arrangement has at least two of the three axes of rotation displaced substantially from the center of the picked part, repositioning of the part to its drop or assembly location may require the fingers to assume a position which impedes or prevents final positioning or assembly.

There is, accordingly, a need for a flexible, general-purpose parts feeder that can handle a large variety of parts without requiring mechanical adjustments or physical alterations to the parts feeder. There is also a need for a parts feeder capable of repetitively presenting parts to a vision system in different orientations, to increase the probability that the parts will be selectable for a work operation.

There is a further need for a parts feeder that avoids jamming problems associated with sliding movement of parts along surfaces, and that can convey parts at a variable speed to present a larger or smaller number of parts, as needed. There is also a need for a simple and easily constructed parts feeder that is compact in size, cost-effective, efficient and readily installed in existing assembly work cells.

SUMMARY OF THE INVENTION

To overcome these and other disadvantages of the prior art, one embodiment of a parts feeder constructed in accordance with the invention includes a transport system for receiving parts and transporting them to a selection zone, and a recirculator that receives non-selected parts from the transport system and recirculates them for receipt and subsequent transport by the transport system through the selection zone. The recirculator is operative to induce the recirculated parts to assume different orientations and/or relative positions for subsequent transport through the selection zone. Preferably, the recirculator tumbles at least some of the non-selected parts onto the transport system so that non-selected parts are repeatedly recirculated through the selection zone in random orientations until they are selected.

In accordance with one aspect of the invention, the transport system includes at least one conveyor, and the recirculator includes a hopper, displaceable between a first position and orientation for receiving non-selected parts conveyed from the selection zone, and a second position and orientation for tumbling such parts onto the at least one conveyor. The hopper advantageously is controllably tipable to tumble a desired percentage of the non-selected parts onto the at least one conveyor.

Another embodiment of a part feeder according to the invention comprises first and second transporters cascaded such that the first transporter receives parts to be transported and tumbles received parts onto the second transporter. The transporters are preferably conveyors, and the second conveyor is preferably driven at a higher speed than the first conveyor, to spread out the parts along the second conveyor and thereby increase the probability that they can be identified and selected. The feeder also includes a third, return transporter that receives non-selected parts that have been transported through the selection zone and conveys them for transfer back to the first transporter. Preferably, the return transporter is arranged so that the non-selected parts are tumbled when they are transferred to and from the return transporter.

In another embodiment, the feeder has first and second transporters cascaded such that the first transporter receives parts to be transported and tumbles received parts onto the second transporter. A selector is also provided, including means for analyzing the orientation of parts in a selection zone and selecting parts according to their orientation.

In accordance with still another aspect of the invention, the parts feeder includes a robot that has a vision system including an optical sensing device for identifying parts as they are conveyed through the selection zone; and that has a gripper for performing a gripping operation on the selected workpieces and transferring the selected workpieces from the conveyor system to a desired location, such as an assembly station.

These and other features of the invention are described in or apparent from the following detailed description of preferred embodiments.

BRIEF DESCRIPTION OF THE DRAWINGS

The preferred embodiments are described with reference to the drawings, in which like reference numerals denote like elements throughout the figures, and in which:

FIG. 1 is a perspective diagrammatic view showing a two-conveyor embodiment of a part feeder according to the invention;

FIG. 2 is a cross-sectional view of a conveyor belt according to the invention;

FIGS. 8(a)–8(c) are front, side and diagrammatic views of a robotic gripper according to another embodiment of the invention;

DETAILED DESCRIPTION OF PREFERRED EMBODIMENTS

Figure 3:
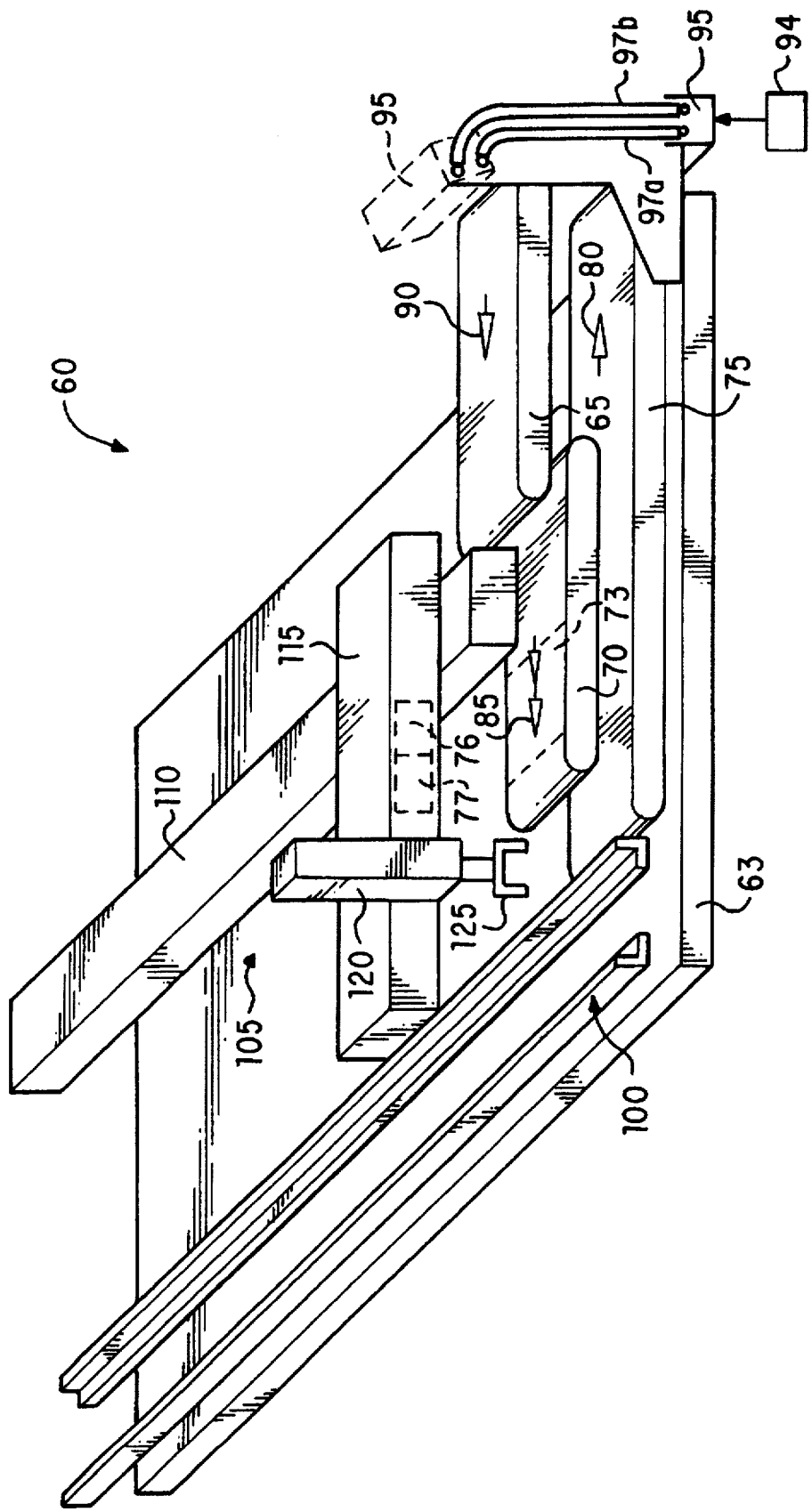
FIG. 3 is a perspective diagrammatic view of a three-conveyor embodiment of a part feeder according to the invention.
Figure 4:
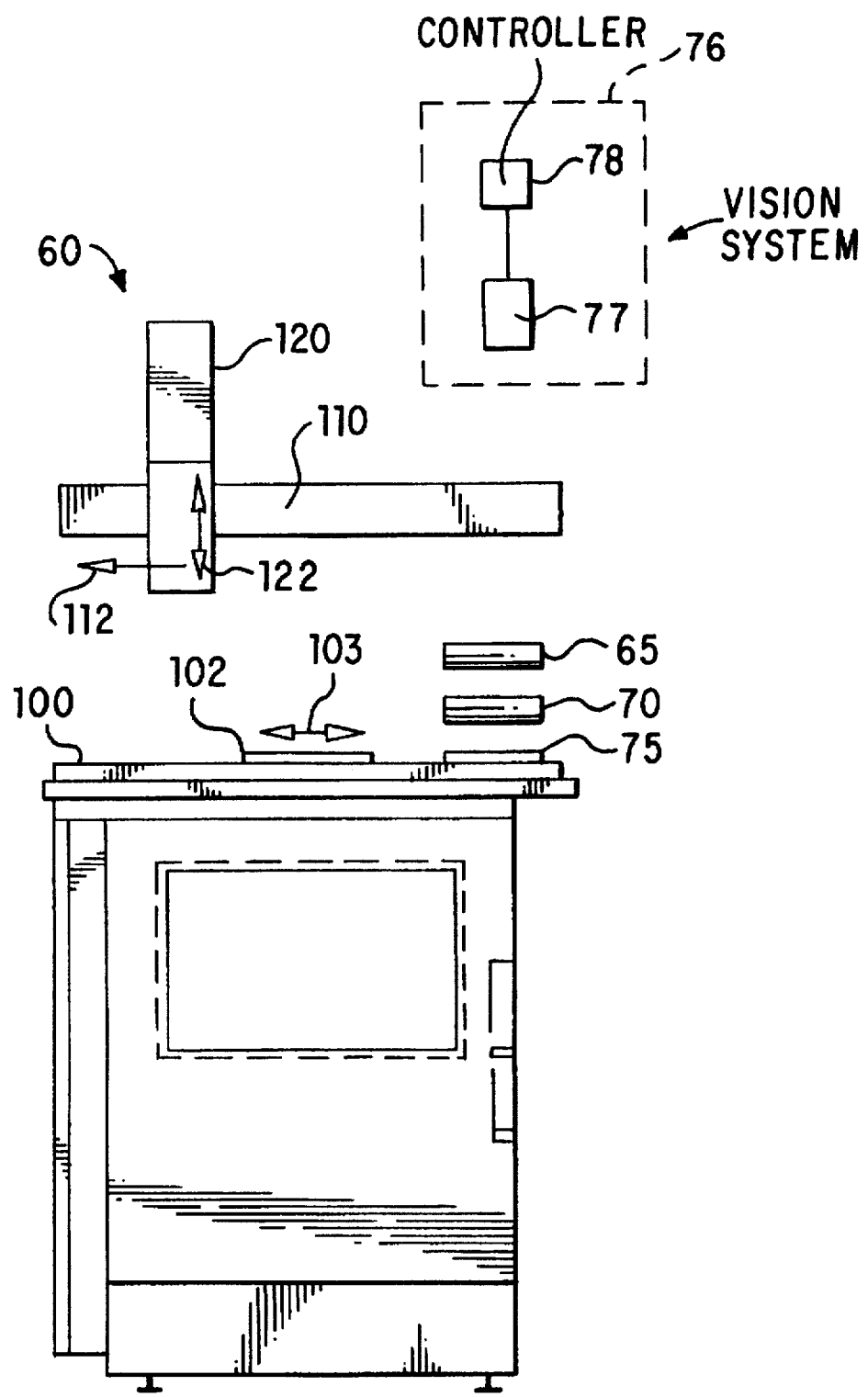
FIG. 4 is a front view of the three-conveyor embodiment shown in FIG. 3.

FIG. 1 depicts a two-conveyor embodiment of the present invention. Parts feeder 5 includes a transport system, including transporter 10. In a preferred embodiment, transporter 10 is a feeding conveyor, which receives parts from another transporter, i.e., buffer conveyor 15, via a slide 40. Feeding conveyor 10 conveys the parts to a predetermined selection zone 13, where a vision system 14, including at least one camera 35 and controller 16, views the parts. The vision system of the aforementioned Roth patent incorporated by reference advantageously constitutes vision system 14. The vision system determines the position and orientation of each part within zone 13 and judges which parts have an orientation permitting them to be gripped and removed from feeding conveyor 10.

Controller 16, which is preferably a microprocessor associated with vision system 14, forms an internal queue of indicia designating those inspected parts having an acceptable orientation and directs a gripping apparatus, such as robot 105 (described below with reference to FIGS. 3–7), to grip each of the queued parts in order. When the queue is exhausted, controller 16 directs conveyor 10 to advance, thereby transferring the remaining, non-selected parts, that is, those parts that cannot be distinguished or having an orientation unsuitable for gripping, to a recirculator such as recirculating hopper 20. Preferably, conveyor 10 is arranged relative to conveyor 15, and conveyor 15 is arranged relative to hopper 20, so that the parts tumble during the transfer between conveyors, and between conveyor 10 and hopper 20.

At least one arm 25 supports hopper 20 for rotational movement about pivot 23. Actuator 30, preferably a pneumatic cylinder, rotates arm 25 about pivot 23 so that hopper 20 moves from the solid-line position of FIG. 1 to the dashed-line position. In the dashed-line position, the parts in hopper 20 are tumbled onto buffer conveyor 15 for recirculation to feeding conveyor 10 and selection zone 13.

Tumbling the parts from hopper 20 to buffer conveyor 15, from buffer conveyor 15 to feeding conveyor 10, and from feeding conveyor 10 to hopper 20 increases the likelihood that recirculated parts will have new orientations and relative positions upon reaching selection zone 13, compared to their orientations and relative positions during previous passes through zone 13. Recirculated parts will eventually have orientations within zone 13 allowing them to be gripped and removed. During the tumbling process, parts are preferably flipped end over end.

The percentage of recirculated parts depends on the particular type of part handled. If, for example, a flat part with only two stable states is handled and only one of those states is acceptable for gripping, then approximately half the parts will be recirculated to buffer conveyor 15 and feeding conveyor 10. Similarly, if six stable states exist (a cube, for example) and only one of those states is acceptable, then potentially 5/6 of those parts will be recirculated. The passed part percentage, therefore, depends on the shape and the center of gravity of the part. It also depends on the gripping device's ability to pick up a part in more than one orientation. The greater are the degrees of freedom that the gripping device has, the greater are the orientations that are acceptable for gripping.

Microprocessor 16 controls movement of conveyors 10, 15, which are driven by independent servomotors. In a preferred embodiment, after conveyor 10 advances parts to selection zone 13, the microprocessor halts conveyors 10, 15 and directs vision system 14 to take a "snapshot" of the parts within the zone. After forming the queue of selected, grippable parts and directing their removal, the microprocessor advances the conveyors to tumble the non-selected parts into hopper 20 for recirculation and bring a next set of parts into zone 13. Alternatively, the microprocessor can select, queue, and direct the removal of grippable parts while conveyor 10 is continuously moving. In either case, the microprocessor halts conveyors 10, 15 during rotation of arm 25. The transport system may also be arranged so that parts are conveyed to selection zone 13 in a manner, for example, spaced batches, permitting rotation of arm 25 while the conveyors are advancing.

Feeding conveyor 10 preferably moves faster than buffer conveyor 15, spreading out the parts tumbled from buffer conveyor 15 and thus increasing the likelihood of part recognition and pick-up in zone 13. Microprocessor 16 controls conveyors 10, 15 independently, so that their relative speeds can be adjusted to alter part spacing on belt 10 and advance a larger or smaller number of parts to zone 13, as desired.

Microprocessor 16 may also control conveyors 10, 15 to operate in a vibratory manner to cause parts on the conveyors to better separate and assume diverse orientations. The conveyors, for example, can be advanced during the first ¾ of a drive cycle and reversed during the final ¼.

In a preferred embodiment, an actuator 31, such as a servomotor, moves hopper 20 relative to supporting arm 25. In the solid-line position of FIG. 1, actuator 31 can position hopper 20 to be partially underneath the downstream edge of feeding conveyor 10, to prevent part misfeed. In the dashed-line position, actuator 31 rotates hopper 20 to provide controlled tipping, so that hopper 20 acts as a second storage buffer (in addition to the buffer formed by conveyor 15 and side rails 45a–c). Hopper 20, for example, could be tipped 20% and then stopped, then tipped 30% and stopped, 40%, etc., thereby tumbling a desired percentage of parts onto buffer conveyor 15 with each incremental rotation.

Microprocessor 16 receives signals from various sensing devices. The servomotors of conveyors 10, 15 have encoders, for example, allowing the microprocessor to continuously monitor the conveyor positions. Hopper 20 has a limit switch for indicating its position relative to arm 25. Actuator 30 has a position sensing mechanism to indicate the location of arm 25. Although vision system 14 preferably determines when hopper 20 is to recirculate, sensors 32 can also be provided to detect when hopper 20 is full. Further, sensors can be provided to determine when buffer conveyor 15 is low on parts.

Although parts can tumble directly from buffer conveyor 15 to feeding conveyor 10, slide 40 is preferred because it promotes tumbling and reduces the tendency of parts to bounce off feeding conveyor 10. Side rails 45a–c also form a bin around buffer conveyor 15, preventing parts tumbled from hopper 20 from falling off buffer conveyor 15. Side rails similar to rails 45a–c also may be provided at the sides of feeding conveyor 10. The side rail height need be no greater than the potential rebound distance of the parts, which is typically no more than 75% of the drop distance.

Parts feeder 5 can feed any type of part that is not damaged by tumbling. Workpieces such as washers, springs, sheet metal stampings, semiconductor components, and circuit board components are examples. The present invention also effectively handles rubber parts, which are sticky and notoriously difficult for prior art bowl feeders to effectively handle.

Unlike the prior art, the part feeder of the invention is quite versatile. Changing from one part type to another requires no mechanical adjustments to or alterations of the physical components of the invention. This represents a significant time and cost savings. Instead, after removing the old parts, an operator makes only a few software-based adjustments to the system operation to ready the feeder for a new type of part. A control panel (not shown) advantageously is provided to facilitate entry of the system changes. The control panel also allows individual components of the system to be selected or deselected, and sliding indicators on the control panel allow individual operating parameters, such as dump delay, feed delay, or feeds/dump, to be set.

As shown in FIG. 2, the upper surface of conveyor belt 50 of conveyors 10, 15 preferably includes molded upstanding projections 55, which aid part advancement. Alternately, the surface of belt 50 may include grooves or other texturing of various depths, for stopping round parts, for example, from rolling on the belt.

FIGS. 3–6 show a second, three-conveyor embodiment of the invention. Three-conveyor parts feeder 60 includes a buffer conveyor 65, which advances parts in the direction of arrow 90 and tumbles them onto feeding conveyor 70. Feeding conveyor 70 then advances the parts in the direction of double arrow 85 to predetermined zone 73. As indicated by double arrow 85, feeding conveyor 70 spreads out the parts by advancing them at a higher speed than buffer conveyor 65, similarly to the FIG. 1 embodiment. Side rails, similar to rails 45a–c of the two-conveyor embodiment, can be also provided to prevent parts from tumbling off conveyors 65, 70, 75.

A microprocessor-controlled vision system 76, similar to vision system 14 of the first embodiment and including at least one camera 77 and controller 78, views parts within selection zone 73 and determines which parts are in an orientation allowing them to be gripped and transferred by robot 105.

Non-selected parts, that is, parts unsuitable for gripping by robot 105, tumble to return conveyor 75, which is supported on base 63. Return conveyor 75 returns the non-selected parts in the direction of arrow 80, tumbling them into hopper 95 for recirculation to buffer conveyor 65. Return conveyor 75 allows the hopper and the robot travel paths to be non-intersecting, thereby allowing the robot and hopper to be operated asynchronously or independently of each other.

Figure 5:
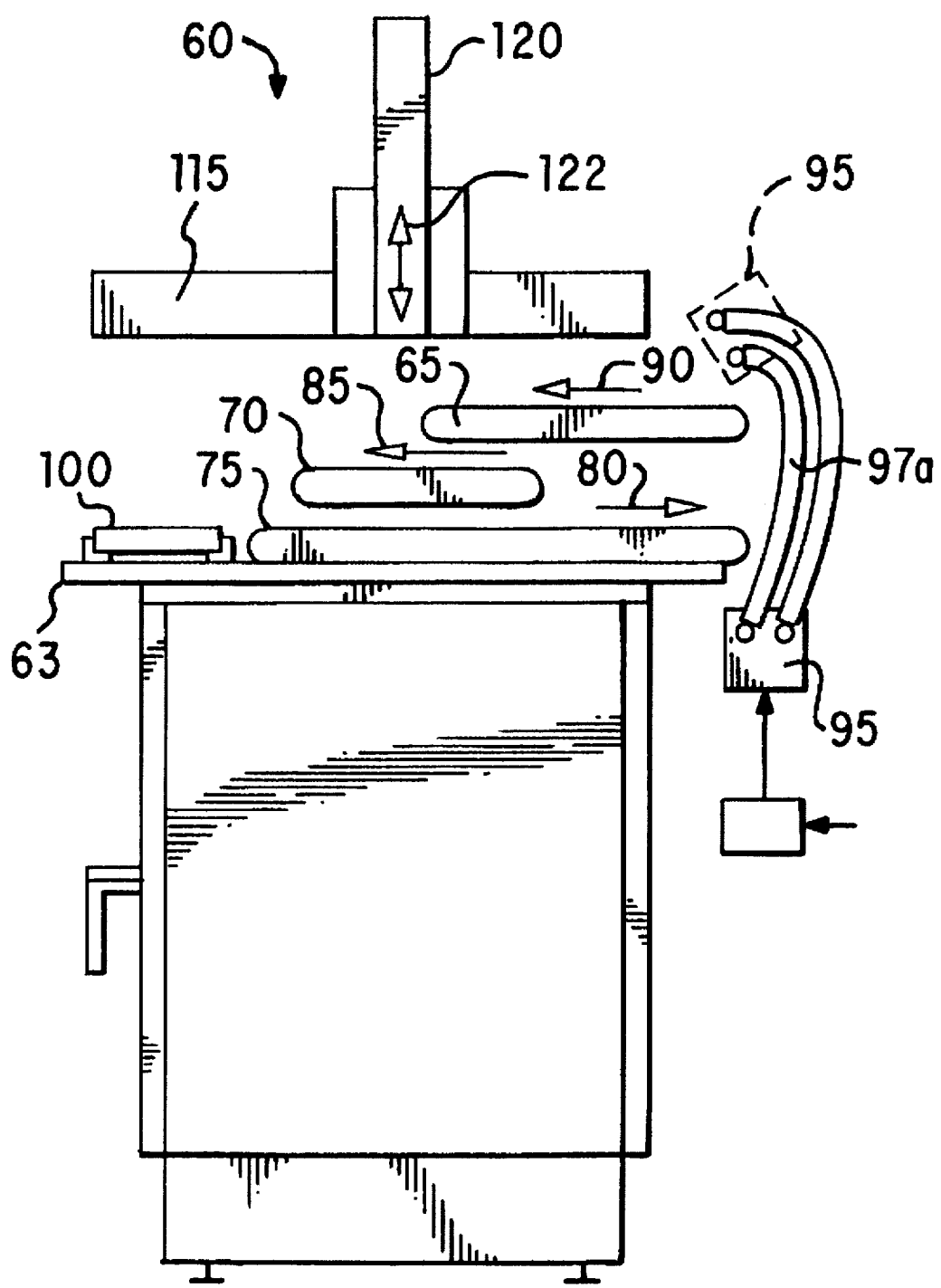
FIG. 5 is a side view of the three-conveyor embodiment shown in FIG. 3.
Figure 6:
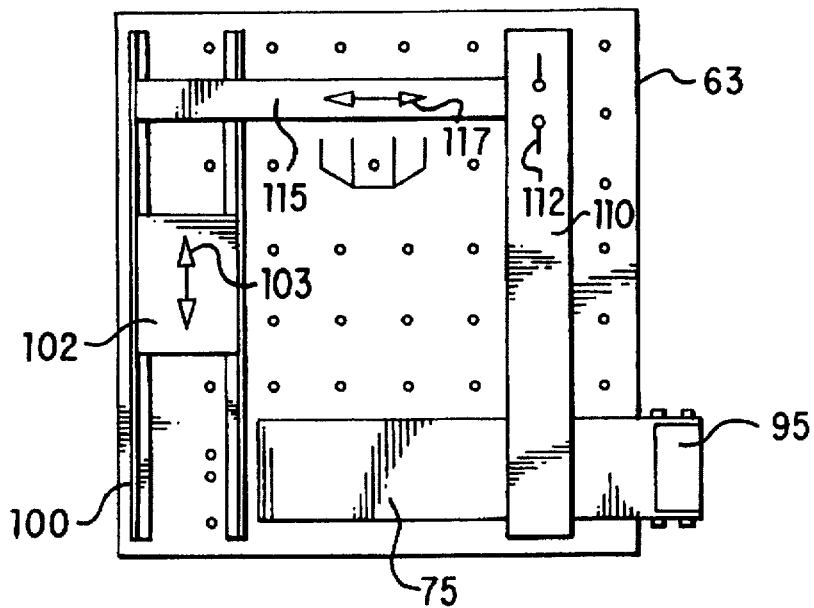
FIG. 6 is a plan view of the three-conveyor embodiment shown in FIG. 3.

Hopper 95 is mounted in rails 97a,b for displacement between a first part-receiving position and orientation (shown in solid lines in FIGS. 3 and 5) adjacent return conveyor 75 and a second part-dispensing position and orientation (shown in dashed lines in FIGS. 3 and 5) adjacent buffer conveyor 65. The upper portions of the rails advantageously are curved, as, shown, to automatically tip hopper 95 as it is displaced upwardly. In addition, the lower portions of the rails may be straight, as shown in FIG. 3, or curved, as shown in FIG. 5. The curved configuration causes hopper 95 to move into an underlapped position relative to return conveyor 75, and into an overlapped position relative to buffer conveyor 65, ensuring that no parts drop from the feeder system during transfer to and from hopper 95.

An actuator 94, such as a servomotor or fluid-operated cylinder, drives hopper 95. Controlled tipping of the hopper is possible, therefore, as in the FIG. 1 embodiment. Tipping may be controlled by merely limiting how far along rails 97a,b hopper 95 is displaced, or by rotating hopper 95 with a separate actuator.

Like the FIG. 1 embodiment, tumbling the parts into and out of hopper 95, as well as between the buffer, feeding, and return conveyors, increases the likelihood that recirculated parts will eventually assume an orientation allowing robot 105 to grip them.

Figure 12:
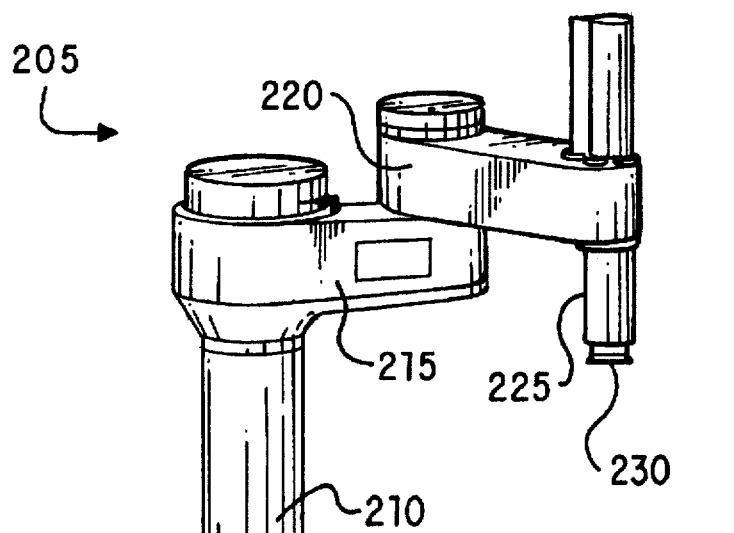
FIG. 12 is a perspective view of a horizontally articulated robot usable with a part feeder according to the invention.

Robot 105 can be either a cartesian-coordinate robot having carriages 110, 115, 120, allowing horizontal movement illustrated by arrows 112, 117 and vertical movement illustrated by arrow 122, or a horizontally articulated robot such as shown in FIG. 12. Gripper 125, depending from a shaft extending from carriage 120, is rotatable about horizontal and vertical axes, allowing parts having various orientations to be gripped. To provide an extra degree of freedom, gripper 125 may include rotating finger pads, as shown, for example, in copending U.S. patent application Ser. No. 08/075,054, which is incorporated herein by reference.

Figure 7:
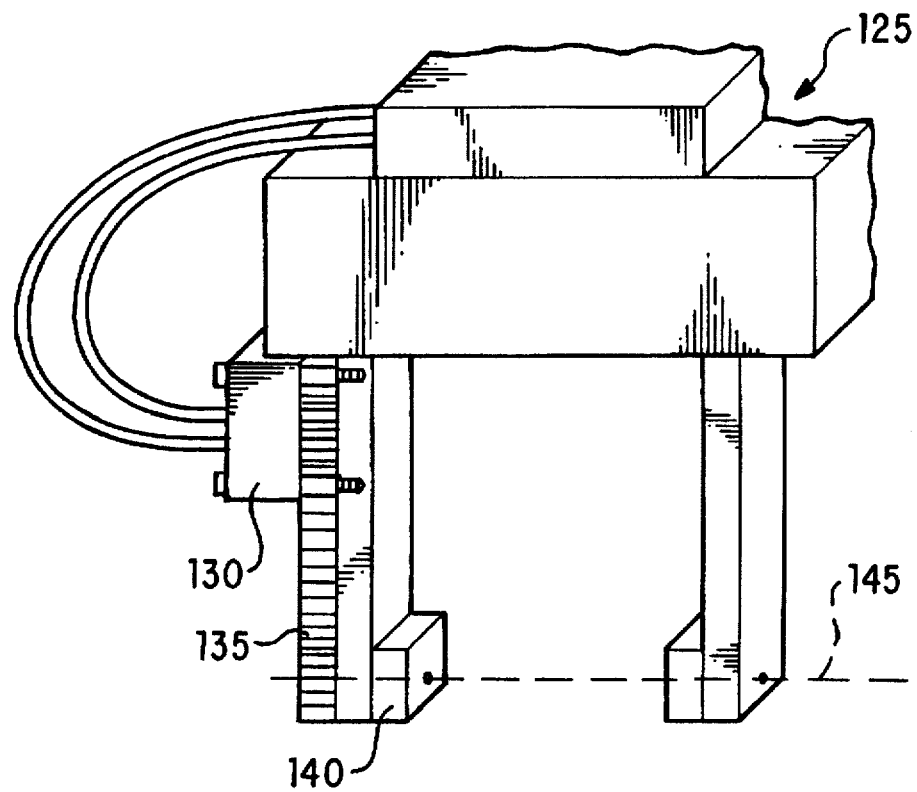
FIG. 7 is a perspective view of a robotic gripper usable in association with the present invention.

FIG. 7 shows another embodiment of gripper 125. Rotary pneumatic actuator 130 has adjustable stops and drives timing chain 135 to rotate pads 140 about axis 145. Rotatable pads 140 provide an extra degree of freedom, allowing parts in a wider variety of orientations to be gripped and removed from the feeding conveyor. Alternatively, pads 140 can be passively rotatable, allowing parts to be picked up along an axis offset from their centers of mass and rotated by gravity to a desired orientation for insertion into a final component.

FIGS. 8a–8c show another embodiment of the gripper. Gripper 125' includes a stepper or servo motor 130' for drivingly rotating one of the rotatable finger pads 140. Motor 130' is connected to the finger pad 140 by a transmission 135'. Transmission 135' includes a first drum 136' coupled to the motor 130' and a second drum 137' coupled to a rotatable finger pad 140. Two steel bands 138',139' are wrapped around the drums to transfer power between the drums. Each band is laser welded, at each end thereof, to the drums. Bands 138' and 139' symmetrically oppose each other about the drums and both bands are in tension. This low friction arrangement eliminates any backlash of the rotatable pad.

Figure 14:
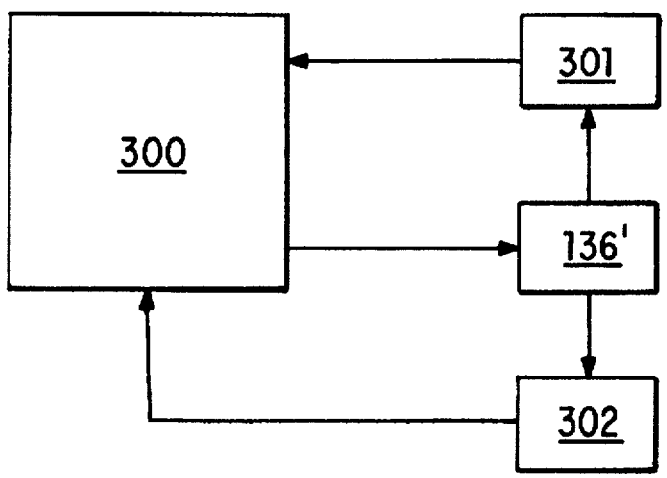
FIG. 14 is a block diagram of the control arrangement for a powered rotating finger gripper arrangement.

The gripper shown in FIGS. 8a–8c can be used to aid in part assembly. The motor current required to rotate the finger pads having a part gripped therebetween is proportional to the gravity and assembly torques acting about the rotational axis of the finger pad. The gravity torque is the result of gravity acting upon the mass of the part and is dependent upon the distance between the rotation axis and the center of mass of the part. As shown in the control block diagram of FIG. 14, the current through the motor 136' is measured by a current measuring device 301, which outputs a signal proportional to the magnitude of the current to a controller 300. Through this arrangement, the controller can determine the gravity torque exerted on the part. Any further torques encounted by the part during movement thereof are "assembly" torques and can be determined by measuring any additional change in the value of the current of the motor 136' by the current measuring device 301. The thus determined assembly torques can then be used to guide the robot to compensate for any part misalignment during assembly. This can be accomplished, for example, in the following manner: upon the detection of an assembly torque, moving the gripper in a predetermined direction or a predetermined pattern for a predetermined distance or until the assembly torque is no longer sensed or until another assembly torque is sensed. The zero backlash, low-friction nature of the transmission permits assembly of parts even with very tight tolerances (e.g. clearances of 0.001").

In a similar manner, the gripper of FIGS. 8a–8c can be used for tactile or touch sensing. For example, the exact location of a hole can be determined by a four axis robot holding a peg. An end of the peg is inserted into the hole at an angle to the axis of the hole. The peg is then rotated in a series of steps about the axis of the finger pad until it contacts the edge of the hole. This contact causes a rise in the current of the motor 136' which is detected by the current detection device 301. The corresponding rotational position of an encoder 302 of the motor is then detected. Based on the encoder position, the contact angle of the peg can be determined. After counter-rotating the peg to clear the edge, the gripper is rotated 120 degrees about the fourth axis of the robot and the operation is repeated. With three such measurements, the center of the hole can be computed.

Figure 9C:
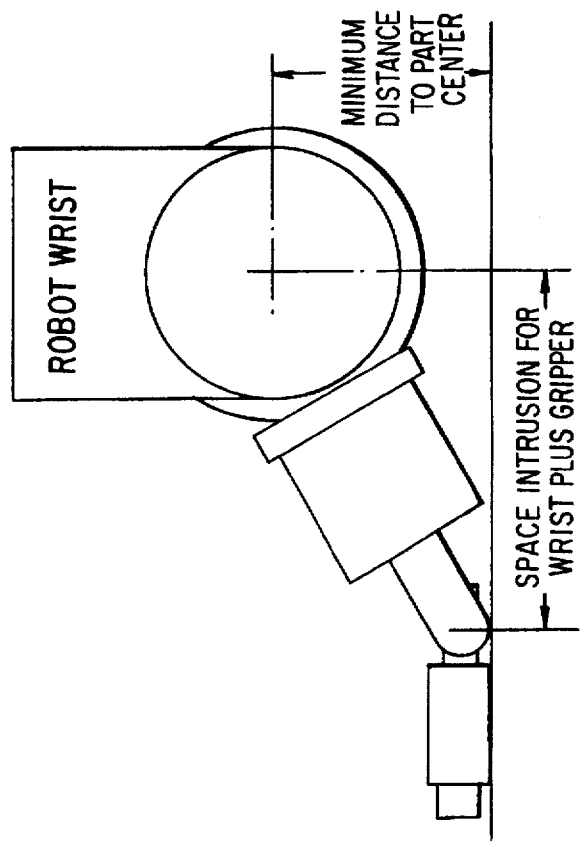
FIGS. 9(a)–9(c) are side views of a passive gripper according to another embodiment of the invention in a respective article gripping and article conveying position.
Figure 9B:
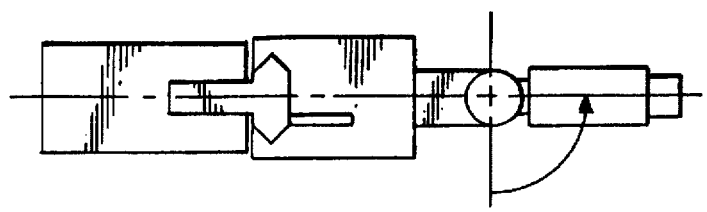
Figure 9A:
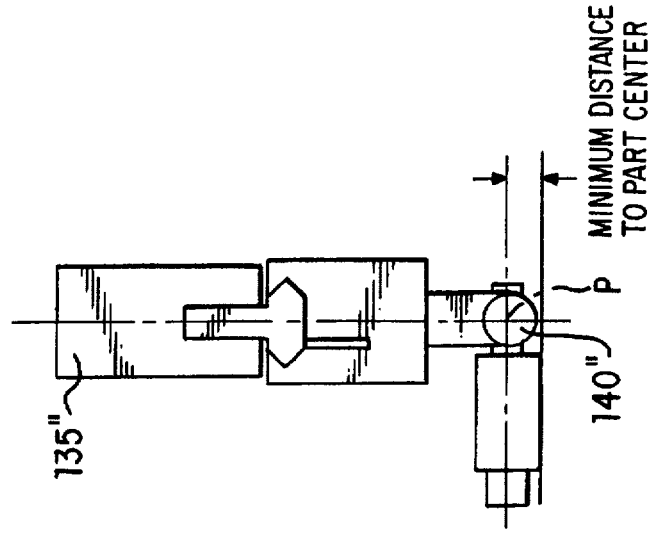

FIGS. 9a–9c show another embodiment of the gripper. Gripper 125" includes passively rotatable finger pads 140" which rotate about a pivot P. FIG. 9a shows a finger pad 140" in contact with one end of a part to be picked up. Because the center of mass of the part is offset from the pivot axis of the finger pads 140", the part is pivoted to its naturally stable gravitational equilibrium orientation shown in FIG. 9b when the part is lifted. As shown in FIG. 9c, the space intrusion for the robot wrist and gripper is minimal.

Common to the gripper embodiments described above is that the rotational axis of the finger pads is provided are very close to the pick-up surface. Ideally, the axis of rotation should be no further from the pick-up surface than the center of the part (i.e. the axis about which the part is to be rotated). This ideal distance approaches zero for very thin parts. This arrangement minimizes the space intrusion of the robot wrist and gripper into the feeding area. Space intrusion is limited to the width of the part plus the finger cross-sections.

Robot 105 transfers parts from feeding conveyor 70 to a desired location. As illustrated in FIGS. 3–6, the robot can transfer parts to a component 102 that can slide in the direction of arrows 103 along feed rails 100. Component 102 may be a printed circuit board, a pallet, or a cassette, for example.

Figure 10:
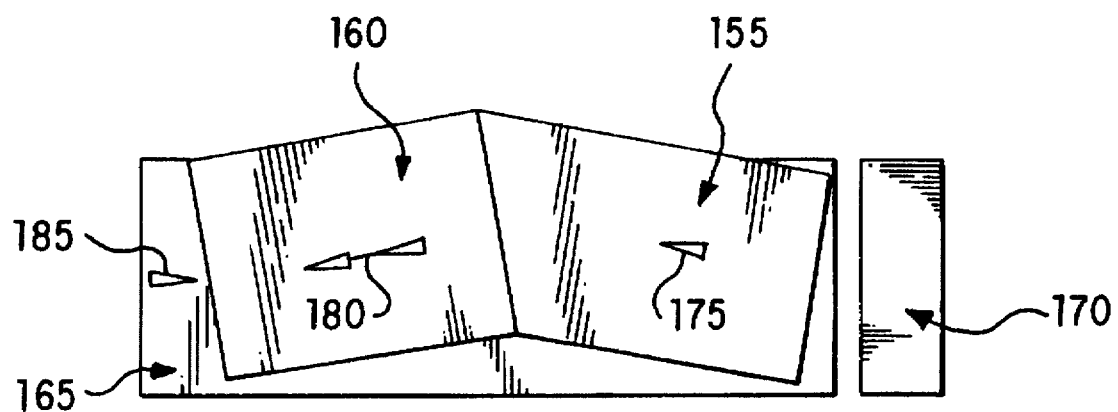
FIG. 10 is a plan view of a second three-conveyor embodiment of a part feeder according to the invention.
Figure 11:
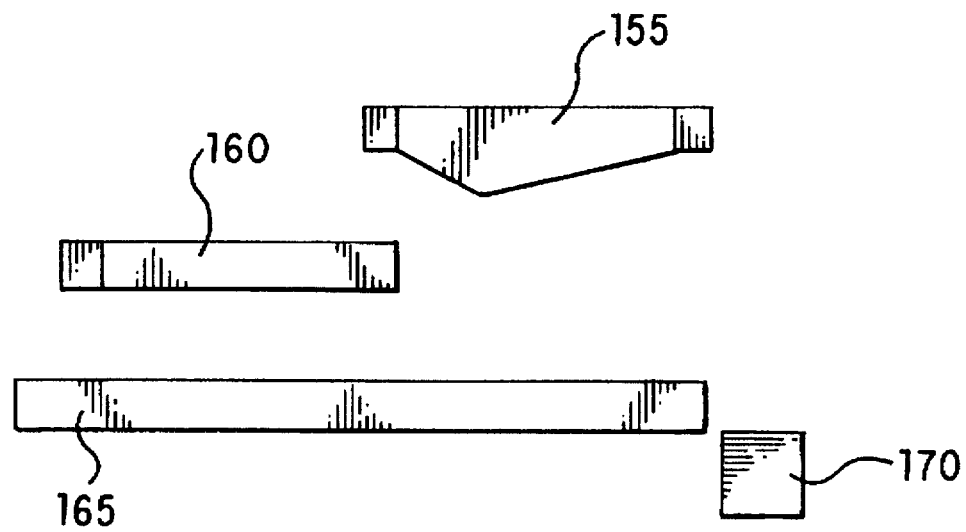
FIG. 11 is a side view of the part feeder shown in FIG. 10.

A third embodiment of the invention is shown in FIGS. 10–11. Buffer conveyor 155 receives parts tumbled from hopper 170 and advances them in the direction of arrow 175 to feeding conveyor 160. Feeding conveyor 160, which is angled with respect to buffer conveyor 155, advances parts in the direction of double arrow 180 and tumbles them onto return conveyor 165, which returns parts in the direction of arrow 185 to hopper 170. As indicated by double arrow 180, feeding conveyor 160 spreads out the parts by advancing them at a higher speed than buffer conveyor 155. Further, because conveyors 155 and 160 are angled with respect to each other, parts on the lower side of buffer conveyor 155 (as viewed in FIG. 10) reach feeding conveyor 160 first and are transported away sooner than parts on the upper side. Parts are separated, therefore, in two dimensions on feeding conveyor 160, instead of in one dimension as in the in-line embodiments of FIGS. 1 and 3-6. Part tumbling occurs between the three conveyors 155, 160, 165 similarly to the tumbling that occurs in the other embodiments, and a vision system similar to that in the other embodiments is also used.

Figure 13:
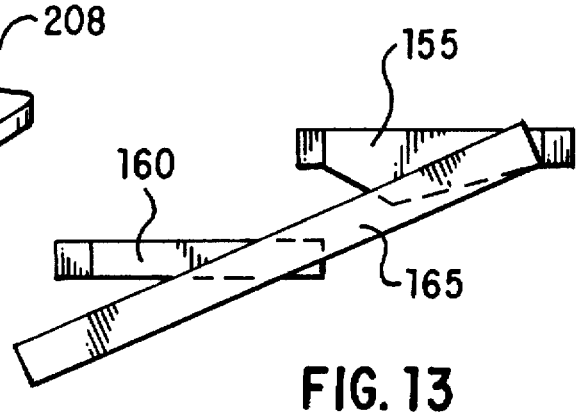
FIG. 13 is a side view of a third three-conveyor embodiment of a part feeder according to the invention.

In an alternate angled-conveyor embodiment as shown in FIG. 13, return conveyor 165 is vertically inclined and has projections or some other mechanism to carry non-selected parts from feeding conveyor 160 to an angled slide (not illustrated). The angled slide returns the non-selected parts to buffer conveyor 155, for eventual deposit on feeding conveyor 160.

FIG. 12 illustrates an alternate robot 205 that can be used in any of the preceding embodiments. Robot 205 includes base 208 and column 210, which supports inner link 215 for horizontal rotational movement. Outer link 220 horizontally rotates on inner link 215 and supports quill 225 for independent rotational movement. User flange 230 allows connection of various end effectors for desired applications.

In each of the feeder embodiments, the robot and conveyors can be driven by software application packages written in a task-level programming language, such as that disclosed in U.S. Pat. No. 4,835,730 to Shimano et al., which is incorporated herein by reference. Program instructions call procedures for approaching, grasping, removing and inserting a part. Databases are accessed to determine part location and approach path, placement location and approach path, motion speeds, the gripper type required to pick up the class of part, etc.

While the invention has been described with reference to specific embodiments, the description is illustrative and is not to be construed as limiting the scope of the invention. For example, and without limitation, it will be appreciated that a part feeding system in accordance with the invention can comprise multiple buffer, feeder and/or return conveyors. Further, the microprocessor-based controller used to control the feeding system can either be dedicated to the part feeder, or a programmable controller associated with the vision system, robot or assembly/work cell with which the part feeder is used. Various other modifications and changes may occur to those skilled in the art without departing from the spirit and scope of the invention.

What is claimed is:

1. A parts feeder, comprising:
   a transport system for receiving parts and transporting the parts to a selection zone at which a selector analyzes parts in the selection zone and selects parts according to the analysis; and
   a recirculator that receives non-selected parts from the transport system and recirculates the received parts for receipt and subsequent transport by said transport system through said selection zone, said recirculator being operative to induce the recirculated parts to assume different orientations and/or relative positions during transport for subsequent passes through said selection zone;
   said recirculator comprising a parts-receptor that moves along a transfer path extending from a location at which the parts-receptor receives non-selected parts from the transport system to a region in which the parts-receptor discharges the received non-selected parts, said transfer path comprising two curved end portions, wherein said parts-receptor is positioned under the transport system when said parts-receptor is at the non-selected parts receiving location.

2. The parts feeder of claim 1, wherein the recirculator tumbles at least some of the recirculated non-selected parts onto the transport system so that non-selected parts are repeatedly recirculated through said selection zone in random orientations and relative positions until the non-selected parts are selected.

3. The parts feeder of claim 2, wherein the transport system includes at least one part-transporting conveyor, and the recirculator includes a hopper, displaceable between a first position and orientation for receiving non-selected parts conveyed by said at least one conveyor from said selection zone, and a second position and orientation for tumbling received non-selected parts onto said at least one conveyor.

4. The parts feeder of claim 3, wherein the recirculator further comprises a controllable hopper displacement system operative to control how many received non-selected parts are tumbled onto said at least one conveyor.

5. The parts feeder of claim 1, wherein said selector comprises means for analyzing the orientation of parts and selecting parts according to their orientation.

6. The parts feeder of claim 1, wherein said transporter system comprise first and second conveyors, at least one of the first and second conveyors having a textured surface tending to prevent parts from moving on the surface.

7. The parts feeder of claim 1, wherein the recirculator comprises at least one curved guide to guide the parts-receptor along the transfer path.

8. The parts feeder of claim 1, further comprising a parts-receptor actuator that controls the amount of non-selected parts discharged by said parts-receptor.

9. The parts feeder of claim 1, wherein said recirculator comprises a guide member for said parts-receptor, said guide member extending from said part-receiving location to said part-discharging region of said transfer path and having at least one curved end portion defining said at least one curved end portion of said transfer path.

10. The parts feeder of claim 1, wherein said selector comprises a gripper for rotating and translating the parts.

11. The parts feeder of claim 10, wherein the gripper comprises rotating finger pads for gripping and rotating the parts about an axis of rotation of at least one of the finger pads.

12. The parts feeder of claim 11, wherein the gripper comprises drive means for driving at least one of the finger pads.

13. The parts feeder of claim 12, wherein the drive means comprises a motor.

14. The parts feeder of claim 13, further comprising means for monitoring the torque of the motor.

15. The parts feeder of claim 14, wherein the torque monitoring means further comprises means for computing torques applied to a gripped part.

16. The parts feeder of claim 15, wherein the torque monitoring means guides the gripper based on the computed torques.

17. The parts feeder of claim 14, wherein the drive means comprises an encoder for detecting the rotational position of an output shaft of the motor, the parts feeder further comprising means for computing when a part contacts another part based on the monitored motor torque.

18. The parts feeder of claim 13, wherein the motor comprises a servo motor.

19. The parts feeder of claim 13, wherein the motor comprises a stepper motor.

20. The parts feeder of claim 13, wherein the drive means comprises a transmission comprising:

at least two drums at least one band wrapped around the drums.

21. The parts feeder of claim 20, wherein the at least one band has two ends respectively fastened to the drums.

22. The parts feeder of claim 11, wherein the rotational axis is spaced from a part support surface no farther than a distance equal to the distance from the center of the part to said support surface when a part is initially gripped by the gripper.

* * * * *